(12) United States Patent
Shabaz

(10) Patent No.: US 9,055,926 B2
(45) Date of Patent: Jun. 16, 2015

(54) GUIDE BLOCK FOR BIOPSY OR SURGICAL DEVICES

(75) Inventor: Martin V. Shabaz, Lake Forest, CA (US)

(73) Assignee: SenoRx, Inc., Tempe, AZ (US)

( * ) Notice: Subject to any disclaimer, the term of this patent is extended or adjusted under 35 U.S.C. 154(b) by 0 days.

(21) Appl. No.: 12/780,643

(22) Filed: May 14, 2010

(65) Prior Publication Data

US 2010/0256521 A1    Oct. 7, 2010

Related U.S. Application Data

(62) Division of application No. 11/981,006, filed on Oct. 31, 2007, now Pat. No. 7,744,543, which is a division of application No. 11/298,154, filed on Dec. 9, 2005, now Pat. No. 7,740,593.

(51) Int. Cl.
| | |
|---|---|
| *A61B 10/00* | (2006.01) |
| *A61N 1/30* | (2006.01) |
| *A61M 31/00* | (2006.01) |
| *A61M 37/00* | (2006.01) |
| *A61B 19/00* | (2006.01) |
| *A61B 17/50* | (2006.01) |
| *A61B 5/00* | (2006.01) |
| *A61B 17/34* | (2006.01) |
| *A61B 5/055* | (2006.01) |
| *A61B 10/02* | (2006.01) |

(52) U.S. Cl.
CPC .............. *A61B 5/708* (2013.01); *A61B 17/3403* (2013.01); *A61B 19/201* (2013.01); *A61B 19/203* (2013.01); *A61B 2017/3411* (2013.01); *A61B 2019/205* (2013.01); *A61B 5/055* (2013.01); *A61B 10/02* (2013.01); *A61B 5/0555* (2013.01); *A61B 10/0233* (2013.01)

(58) Field of Classification Search
CPC ............................................... A61B 2017/3411
USPC ........... 600/562, 564; 604/19, 48, 93.01, 116; 606/130, 131, 96, 98
See application file for complete search history.

(56) References Cited

U.S. PATENT DOCUMENTS

| | | | |
|---|---|---|---|
| 3,039,386 A | | 6/1962 | Trisler |
| 3,721,218 A | | 3/1973 | Null |
| 3,844,272 A | | 10/1974 | Banko |
| 3,927,660 A | | 12/1975 | Tegtmeyer |
| 3,955,558 A | * | 5/1976 | Fuisz ........................... 600/573 |
| 4,029,084 A | | 6/1977 | Soldner |

(Continued)

FOREIGN PATENT DOCUMENTS

| | | |
|---|---|---|
| DE | 4442609 C1 | 8/1996 |
| DE | 29519103 U1 | 1/1997 |

(Continued)

*Primary Examiner* — Sean Dougherty

(57) ABSTRACT

One embodiment having features of the invention is directed to a guide block for an MRI device which has a block body with a proximal face, a distal face, and four parallel passageways extending between the two faces. The first passageway is centrally disposed, the second passageway is disposed vertical or horizontal to the first, the third passageway is located diagonal to the first and has a longitudinal opening in fluid communication with the first passageway, and the fourth passageway is diagonal to the first and in an opposite side of the body from the third passageway. In an alternative embodiment the guide block has at least one passageway that is not parallel to the longitudinal axis.

6 Claims, 4 Drawing Sheets

(56) References Cited

U.S. PATENT DOCUMENTS

| | | | |
|---|---|---|---|
| 4,228,796 A | | 10/1980 | Gardiner |
| 4,289,139 A | * | 9/1981 | Enjoji et al. ............... 600/461 |
| 4,629,451 A | * | 12/1986 | Winters et al. ............. 604/175 |
| 4,642,096 A | | 2/1987 | Katz |
| 4,798,212 A | | 1/1989 | Arana |
| 4,911,395 A | | 3/1990 | Jones, Jr. |
| 4,943,986 A | | 7/1990 | Barbarisi |
| 4,952,214 A | | 8/1990 | Comparetto |
| 4,998,912 A | * | 3/1991 | Scarbrough et al. .............. 600/6 |
| 5,078,719 A | | 1/1992 | Schreiber |
| 5,098,383 A | | 3/1992 | Hemmy et al. |
| 5,105,457 A | | 4/1992 | Glassman |
| 5,110,660 A | | 5/1992 | Wolf et al. |
| 5,254,119 A | | 10/1993 | Schreiber |
| 5,306,278 A | * | 4/1994 | Dahl et al. ................... 606/96 |
| 5,335,671 A | | 8/1994 | Clement |
| 5,349,871 A | | 9/1994 | Naganuma |
| 5,417,695 A | * | 5/1995 | Axelson, Jr. ................. 606/89 |
| 5,449,360 A | * | 9/1995 | Schreiber .................... 606/87 |
| 5,514,140 A | * | 5/1996 | Lackey ...................... 606/80 |
| 5,653,723 A | | 8/1997 | Kamerling et al. |
| 5,690,108 A | | 11/1997 | Chakeres |
| 5,702,405 A | * | 12/1997 | Heywang-Koebrunner . 606/130 |
| 5,741,251 A | | 4/1998 | Benoist |
| 5,846,212 A | | 12/1998 | Beeuwkes et al. |
| 5,855,554 A | * | 1/1999 | Schneider et al. ........... 600/407 |
| 5,904,691 A | | 5/1999 | Barnett et al. |
| 5,913,863 A | * | 6/1999 | Fischer et al. ............... 606/130 |
| 5,957,935 A | * | 9/1999 | Brown et al. ............... 606/130 |
| 5,971,998 A | * | 10/1999 | Russell et al. .............. 606/130 |
| 6,036,632 A | * | 3/2000 | Whitmore et al. .............. 600/7 |
| 6,066,131 A | | 5/2000 | Mueller et al. |
| 6,206,832 B1 | * | 3/2001 | Downey et al. ............. 600/439 |
| 6,416,528 B1 | | 7/2002 | Michelson |
| 6,458,074 B1 | | 10/2002 | Matsui et al. |
| 6,461,296 B1 | * | 10/2002 | Desai ........................... 600/210 |
| 6,478,799 B1 | * | 11/2002 | Williamson ................. 606/90 |
| 6,500,109 B2 | * | 12/2002 | Tokita et al. ................... 600/7 |
| 6,508,786 B2 | | 1/2003 | Huitema et al. |
| 6,530,922 B2 | * | 3/2003 | Cosman et al. .............. 606/34 |
| 6,551,275 B2 | | 4/2003 | Fontayne et al. |
| 6,579,262 B1 | | 6/2003 | Mick et al. |
| 6,589,242 B1 | * | 7/2003 | Feiler .......................... 606/56 |
| 6,846,315 B2 | * | 1/2005 | Barzell et al. ................ 606/130 |
| 6,913,463 B2 | | 7/2005 | Blacklock |
| 7,204,209 B2 | | 4/2007 | Marin et al. |
| 7,235,084 B2 | | 6/2007 | Skakoon et al. |
| 7,255,682 B1 | | 8/2007 | Bartol et al. |
| 7,379,769 B2 | * | 5/2008 | Piron et al. ................... 600/415 |
| 7,419,499 B2 | | 9/2008 | Dalton |
| 7,507,210 B2 | * | 3/2009 | Hibner et al. ............... 600/567 |
| 7,549,424 B2 | * | 6/2009 | Desai ........................... 128/898 |
| 7,658,879 B2 | * | 2/2010 | Solar ........................... 264/278 |
| 8,057,432 B2 | * | 11/2011 | Flagle et al. ................. 604/116 |
| 8,273,091 B2 | * | 9/2012 | Elghazaly ..................... 606/96 |
| 8,398,565 B2 | | 3/2013 | Shabaz |
| 8,758,265 B2 | | 6/2014 | Shabaz |
| 2002/0058939 A1 | | 5/2002 | Wagner et al. |
| 2002/0128716 A1 | | 9/2002 | Cohen et al. |
| 2003/0060828 A1 | | 3/2003 | Michelson |
| 2004/0143150 A1 | * | 7/2004 | Barzell et al. ..................... 600/7 |
| 2004/0167543 A1 | | 8/2004 | Mazzocchi et al. |
| 2005/0101868 A1 | * | 5/2005 | Ridley et al. ............... 600/459 |
| 2005/0182407 A1 | | 8/2005 | Dalton |
| 2005/0283069 A1 | * | 12/2005 | Hughes et al. .............. 600/423 |
| 2006/0155291 A1 | * | 7/2006 | Farrar et al. ................... 606/87 |
| 2007/0233157 A1 | | 10/2007 | Mark et al. .................. 606/130 |
| 2007/0255168 A1 | * | 11/2007 | Hibner et al. ............... 600/562 |
| 2007/0282451 A1 | | 12/2007 | Metzger et al. |
| 2008/0161669 A1 | | 7/2008 | Hauck et al. |
| 2009/0018437 A1 | | 1/2009 | Cooke |
| 2009/0138018 A1 | | 5/2009 | Haines |
| 2009/0163830 A1 | * | 6/2009 | Hibner et al. ............... 600/567 |
| 2009/0292224 A1 | * | 11/2009 | Bowman et al. ........... 600/567 |
| 2009/0292244 A1 | * | 11/2009 | Flagle et al. ................. 604/116 |
| 2010/0179532 A1 | * | 7/2010 | Buysse et al. ................. 606/33 |

FOREIGN PATENT DOCUMENTS

| | | | | |
|---|---|---|---|---|
| EP | 0 682 916 | | 11/1995 | |
| EP | 0832609 A2 | | 4/1998 | |
| EP | 1 219 269 | | 7/2002 | |
| WO | WO 01/17585 | | 3/2001 | |
| WO | 0213709 A1 | | 2/2002 | |
| WO | WO 03/039386 | | 5/2003 | |
| WO | WO 0309386 A1 | * | 5/2003 | ............ A61B 19/00 |
| WO | WO 2004/017842 | | 3/2004 | |
| WO | WO 2004/051409 | | 6/2004 | |

* cited by examiner

GUIDE BLOCK FOR BIOPSY OR SURGICAL DEVICES

This application is a divisional of application Ser. No. 11/981,006, filed Oct. 31, 2007, now U.S. Pat. No. 7,744,543, which is a divisional of application Ser. No. 11/298,154, filed Dec. 9, 2005, now U.S. Pat. No. 7,740,593, all of which are incorporated herein in their entirety by reference and from which priority is claimed.

FIELD OF THE INVENTION

This invention relates generally to the field of medical devices and methods. In particular, the invention relates to devices and methods for placing a surgical device, such as a biopsy device, in a desired location in relation to a patient during a biopsy procedure.

BACKGROUND OF THE INVENTION

In diagnosing and treating certain medical conditions, it is often desirable to perform a biopsy, in which a specimen or sample of tissue is removed for pathological examination, tests and analysis. As is known, obtaining a tissue sample by biopsy and the subsequent examination are typically employed in the diagnosis of cancers and other malignant tumors, or to confirm that a suspected lesion or tumor is not malignant. Examination of tissue samples taken by biopsy is of particular significance in the diagnosis and treatment of breast cancer.

Magnetic resonance imaging (MRI) is often used to locate the site within a breast where a potentially cancerous lesion or tumor is located. Interventional MRI is the magnetic resonance imaging technique (often involving real time imaging) that allows a surgeon to perform MRI-guided tissue biopsy or surgery. One application of interventional MRI is to guide a surgeon during a biopsy or surgical operation on one or both of the breasts of a female patient.

Interventional MRI procedures typically require a magnetic resonance signal detection coil which has large openings so that the surgeon can have access to the surgical site through the coil with the biopsy device or other surgical devices. The MRI device may also include compression plates to compress the breast. Compression plates contain needle guide holes to allow for proper placement of a needle during a needle biopsy or larger windows configured to hold guide blocks. Guide blocks have block bodies with needle guide holes or with larger openings to allow access for larger biopsy devices. The guide blocks assist the physician with proper placement and stabilization of the biopsy device during a biopsy procedure.

The compression plates are secured to the housing of the signal detection coil. Markers, such as Vitamin E Capsules, which are highly visible under MRI device are placed on the compression plates and the position of the markers relative to the suspect tissue is measured using the magnetic resonance images. The proper window of the compression plate is then determined by finding the window in the compression plate which is closest to the desired entry point.

For larger biopsy devices the guide blocks are usually cube-shaped and contain about nine circular openings spaced in three rows of three. Due to the configuration of the openings in the guide block and the large size of some biopsy devices it is often difficult to precisely reach the desired tissue location. Present guide blocks for larger biopsy devices do not allow for access to every area of tissue directly behind the block. Thus, there is need in the art for improved guide blocks which allow access to all areas of tissue directly behind the block.

SUMMARY OF THE INVENTION

This invention relates to placement of surgical devices during biopsy procedures and in particular to devices and methods for placement of a biopsy device during a breast biopsy.

In one embodiment of the present invention a guide block has a body with a proximal face, a distal face and a longitudinal axis extending between the proximal and distal faces. The guide block has four passageways which are configured to slidably receive a surgical device, such as a biopsy device. The body of the guide block is configured to fit within a grid on the compression plate of a magnetic resonance imaging (MRI) device.

The four passageways extend longitudinally between the proximal and distal faces of the block and are parallel to the longitudinal axis. The first passageway is centrally disposed. The second passageway is located vertical or horizontal to the first passageway. The third passageway is located diagonal to the first and has a longitudinal opening along its length which is in fluid communication with the opening in the first passageway. The fourth passageway is located diagonal to the first passageway and on an opposite side of the body from the third passageway. The configuration of the passageways allows for all tissue directly behind the guide block to be accessed by rotating the guide block.

A method embodying features of the invention includes providing a guide block having a body with four passageways which are configured within the body as described above and inserting the guide block into a grid opening of a magnetic resonance imaging device nearest to the suspect tissue and orienting the block to provide access to the desired location in a patient.

In an alternative embodiment of the invention a guide block has a block body with a proximal face, a distal face, and a longitudinal axis extending between the proximal and distal faces. The guide block has at least one passageway disposed within the body which is open along the length thereof and which extends between the proximal and distal faces and are not parallel to the longitudinal axis. The configuration of the at least one passageway allows for access to tissue located outside of the exterior border of the compression plate.

A method embodying features of the invention includes providing a guide block having a body with a proximal face, a distal face, and a longitudinal axis extending between the proximal and distal faces. The guide block has at least one passageway disposed within the body which extends between the proximal and distal faces and which is not parallel to the longitudinal axis. The method further includes inserting the guide block into a grid opening of an MRI nearest to the suspect tissue and selecting the orientation of the block 10 to provide access to the desired location in the patient.

DETAILED DESCRIPTION OF THE INVENTION

Figure 1:
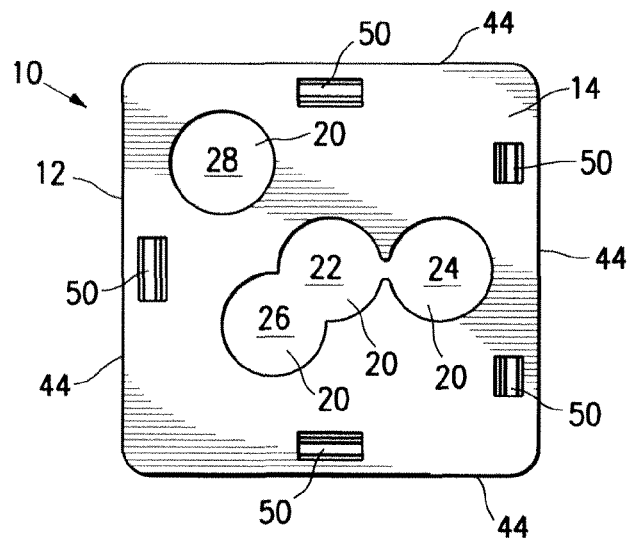
FIG. 1 is a front elevational view of a device embodying features of the invention.

FIGS. 1-6 are elevational views of devices embodying features of the invention. A device embodying features of the invention includes a guide block 10 having a body 12 with a proximal face 14, a distal face 16 and a longitudinal axis 18 extending between the proximal 14 and distal 16 faces. The guide block 10 has four passageways 20 which extend longitudinally between the proximal 14 and distal 16 faces of the guide block 10 and which are parallel to the longitudinal axis 18. Each passageway 20 of the guide block 10 is configured to slidably receive a surgical device, such as the biopsy device in U.S. Pat. No. 6,454,727 assigned to the assignee of the present invention. Preferably the passageways 20 are cylindrically shaped.

Figure 2:
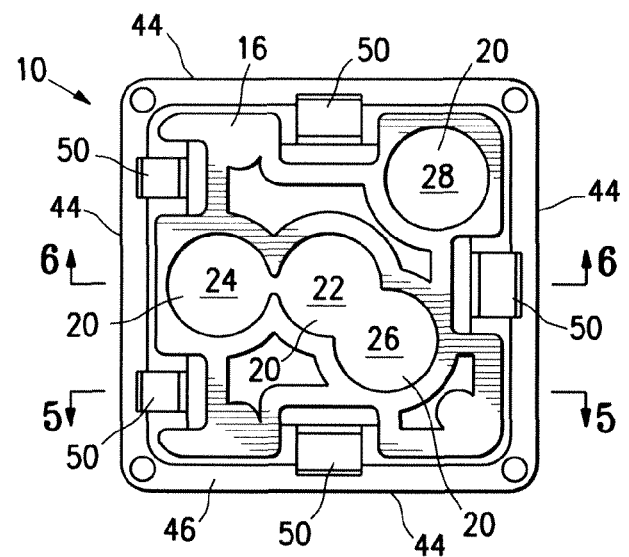
FIG. 2 is a rear elevational view of a device embodying features of the invention.
Figure 3:
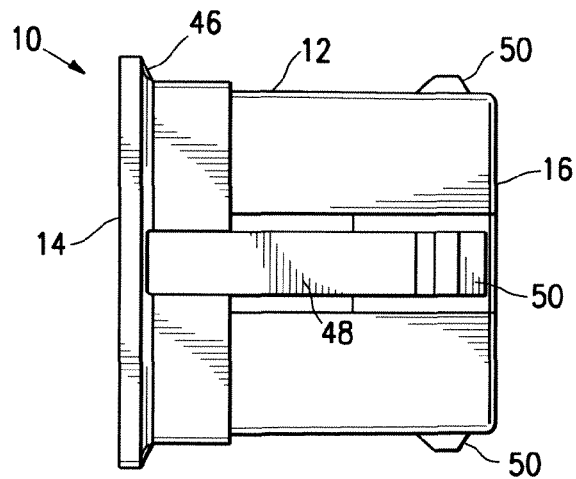
FIG. 3 is a side elevational view of a device embodying features of the invention.
Figure 4:
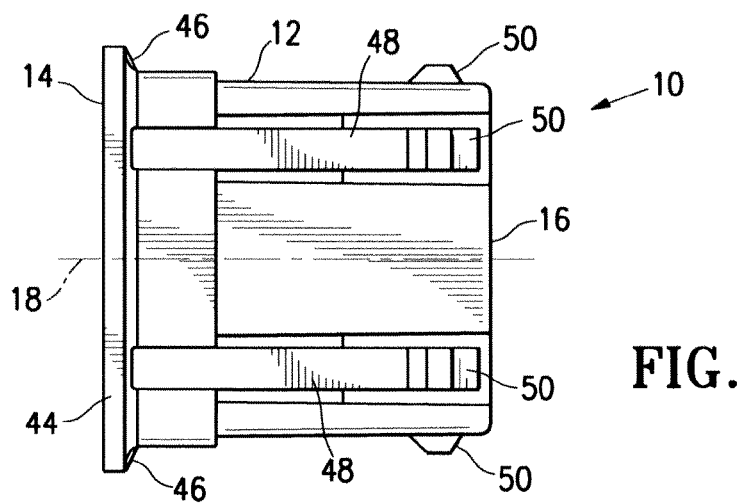
FIG. 4 is a side elevational view of a device embodying features of the invention.
Figure 5:
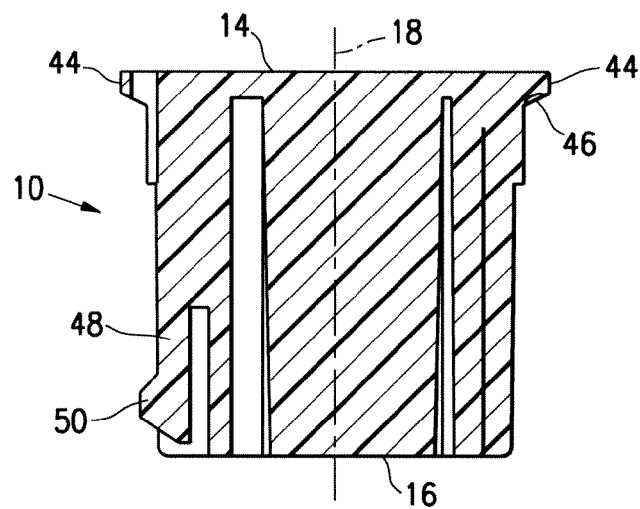
FIG. 5 is a longitudinal cross sectional view of the device taken along lines 5-5 in FIG. 2.
Figure 6:
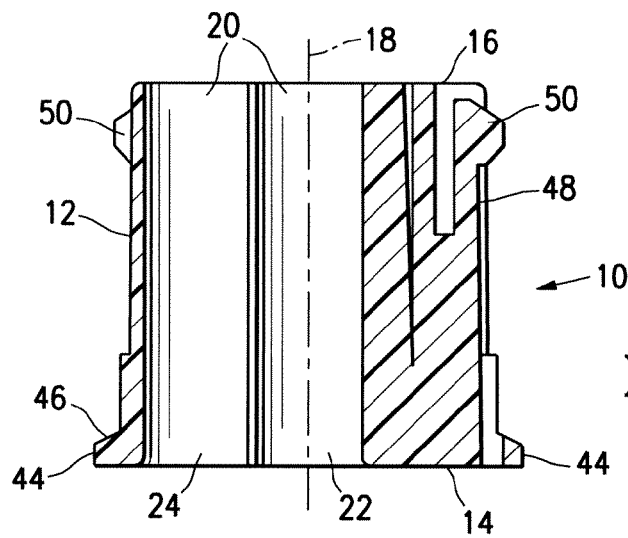
FIG. 6 is a longitudinal cross sectional view of the device taken along lines 6-6 in FIG. 2.

The first passageway 22 is centrally disposed. The second passageway 24 is located vertical or horizontal to the first passageway 22 and parallel to the longitudinal axis. The third passageway 26 is located diagonal to the first passageway 22, and is parallel to the longitudinal axis. The third passageway also has a longitudinal opening along its length which is in fluid communication with the opening in the first passageway 22. The fourth passageway 28, is parallel to the longitudinal axis, and is located diagonal to the first passageway 22 and in an opposite side of the body 12 from the diagonal location of the third passageway 26. Two suitable configurations of the passageways 20 within the guide block 10, shown in FIGS. 1 and 2, are mirror images of one another.

Figure 7:
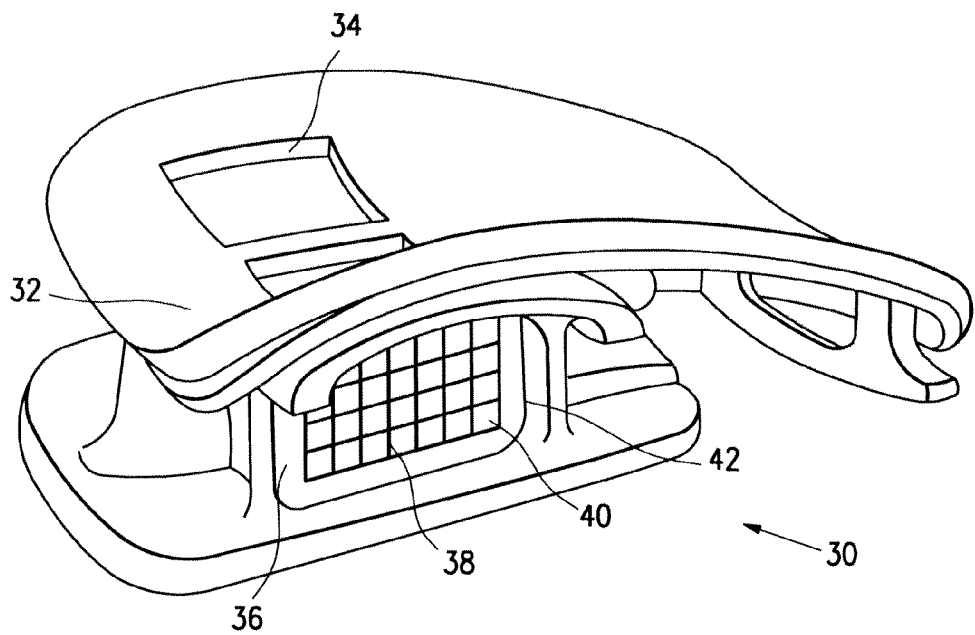
FIG. 7 is a elevational view of a magnetic resonance imaging device having compression plates with grids configured to receive devices embodying features of the invention.
Figure 8:
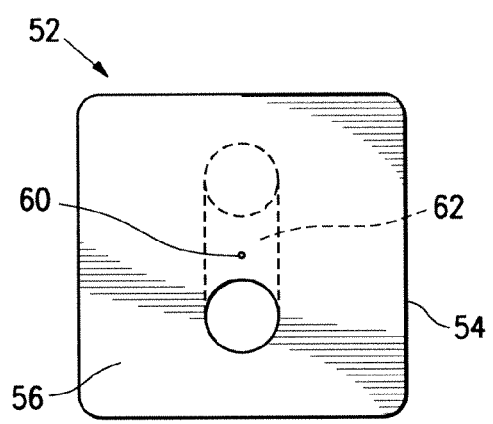
FIG. 8 is a front elevational view of a device embodying features of the invention.
Figure 9:
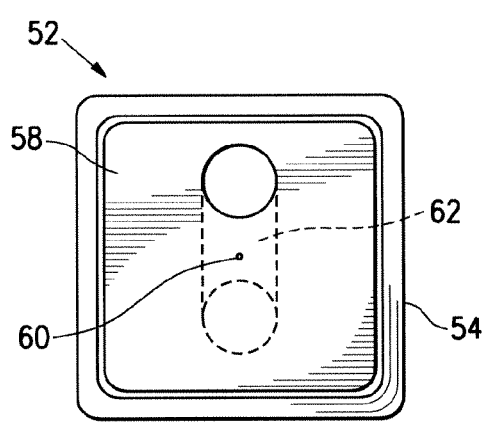
FIG. 9 is a rear elevational view of a device embodying features of the invention.
Figure 10:
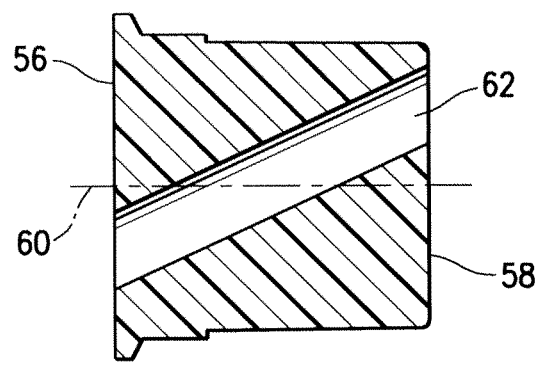
FIG. 10 is a longitudinal cross sectional view of a device shown in FIGS. 8 and 9.
Figure 11:
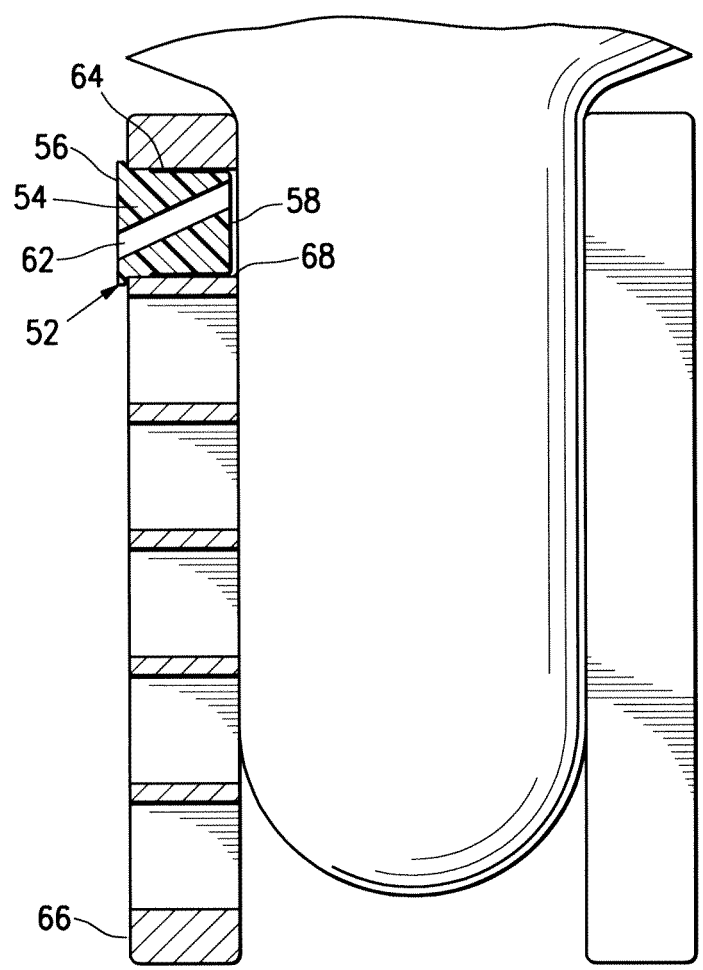
FIG. 11 is a side view of a device embodying features of the invention within the grid of a compression plate.

The guide block 10 is configured to be used in conjunction with a locating or imaging devices such as a magnetic resonance imaging (MRI) device. An example of an MRI breast coil and grid device is the Invivo 7 channel breast biopsy array 800239 in FIG. 7 (photo obtained from www.mridevices.com/products/CoilProduct_Detail.aspx?ID=43). A MRI device 30 used to detect suspect tissue in breasts has a detection coil 32 with large openings 34. The MRI device 30 also includes compression plates 36 to compress the breast. The compression plates 36 are secured to the housing of the detection coil 32 and include grid 38 with grid openings 40 so that the surgeon can have access to the surgical site through the coil 32 with the biopsy device or other surgical devices. The grid openings 40 have four sides 42 and are configured to receive the guide blocks 10 and hold them in place. Preferably the guide block 10 has a proximal face 14 with four equal sides 44. When the guide block 10 is placed into the grid opening 40 any one of the four sides 44 of the proximal face 14 of the guide block may align with any one of the four sides 42 of a grid opening 40 to secure the block within the grid 38.

The location of the passageways 20 within the block 10 allows a biopsy device to gain access to all areas of tissue behind the block 10. By rotating the block before placing it within the grid opening 40, each area of tissue behind the block 10 will, at some point, be accessible through one of the four passageways 20.

In some embodiments the proximal face 14 has a larger surface area than the surface area of the distal face 16 and forms a radially projecting shoulder 46 which prevents the block from advancing too far past the grid opening 40. The shoulder 46 extends about 0.02 inches to about 0.06 inches from the outside wall of the body.

In one embodiment of the device each side 44 of the proximal face 14 of the device is about 0.4 inches to about 1.3 inches long, typically about 0.9 inches long. In this embodiment the center of the first passageway 22 is about 0.2 inches to about 0.6 inches from each side 44 of the proximal face, typically about 0.4 inches from each side 44. The center of the second passageway 24 is about to 0.1 inches about 0.35 inches from the center of the first passageway 22, typically about 0.2 inches away from the center of the first passageway 22. The center of the third passageway 26 is about 0.1 inches to about 0.25 inches, typically about 0.15 inches away from the center of the first passageway 22. The center of the fourth passageway 28 is about 0.15 inches to about 0.5 inches away from the center of the first guide passageway 22, typically about 0.3 inches. The length of block 10 is about 0.5 to about 0.9, typically about 0.8 inches.

In one embodiment the guide block 10 includes at least one tab 48 on the perimeter of the body which extends between the proximal and distal faces and which has a distal portion near the distal face of the block with a raised area 50. The tabs 48 are configured to allow the raised area 50 to bend inward toward the body when placing the block within a grid opening 40. Once in the opening the raised area 50 extends radially outward and presses against the sides 42 of the grid opening 40 as a means to maintain its position.

In some embodiments the tab is about 0.05 inches to about 0.15 inches wide, preferably about 0.10 inches wide. The tabs range in length from about 0.25 to about 0.8 inches long. In some embodiments of the invention at least one tab 48 is about 0.05 to about 0.2 inches wide, preferably about 0.15 inches wide.

The guide block 10 may be formed from a plastic such as MAKROLON®, a polycarbonate from Bayer Material Sciences a division of Bayer AG.

A method embodying features of the invention includes providing a guide block 10 having a body 12 with four passageways 20 which are configured within the body. The first passageway 22 is centrally disposed. The second passageway 24 is located vertical or horizontal to the first passageway 22 and parallel to the longitudinal axis. The third passageway 26 is located diagonal to the first passageway 22, and is parallel to the longitudinal axis. The third passageway also has a longitudinal opening along its length which is in fluid communication with the opening in the first passageway 22. The fourth passageway 28, is parallel to the longitudinal axis, and is located diagonal to the first passageway 22 and in on opposite side of the body 12 from the diagonal location of the third passageway 26. The method further includes inserting the guide block into a grid opening 40 of an MRI device 30 nearest to the suspect tissue and selecting the orientation of the block 10 to provide access to the desired location in patient.

In some methods embodying features of the invention an imaging device configured to locate suspect tissue is provided to locate the suspect tissue. Preferably the imaging device is magnetic resonance imaging 30.

An alternative embodiment of the invention illustrated in FIGS. 8-11 include a guide block 52 having a body 54 with a proximal face 56, a distal face 58, and a longitudinal axis 60 extending between the proximal face 56 and distal face 58. The guide block 52 has at least one passageway 62 disposed within the body which extends between the proximal and distal faces and are not parallel to the longitudinal axis. This embodiment provides access to tissue located outside of the exterior border of the grid 64 of the compression plate 66.

A method embodying features of the invention includes providing a guide block 52 having a body 54 with a proximal face 56 a distal face 58, and a longitudinal axis 60 extending between the proximal and distal faces. The guide block 52 has at least one passageway 62 disposed within the body 54 which extends between the proximal 56 and distal faces 58 and which is not parallel to the longitudinal axis 60. The method further includes inserting the guide block 52 into a grid opening 68 of a compression plate 66 nearest to the suspect tissue and selecting the orientation of the block 52 to provide access to the desired location in the patient.

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "portion", "section", "steps", "means" and words of similar import when used herein shall not be construed as invoking the provisions of 35 U.S.C §112(6) unless the following claims expressly use the terms "means" or "step" followed by a particular function without reference to a specific structure or action. All patents and all patent applications referred to above are hereby incorporated by reference in their entirety.

What is claimed is:

1. A guide block and grid-like breast receiving pressure plate assembly for a tissue removing device, comprising:
   a. a guide block having a proximal face with at least a first proximal opening, a distal face with at least a first distal opening, a body length between the proximal and distal faces with a central longitudinal axis extending within the guide block between the proximal and distal faces, a first passageway configured to extend within the guide block between the first proximal opening in the proximal face and the first distal opening in the distal face, the first passageway being oriented at an angle with respect to the central longitudinal axis that is not parallel to the central longitudinal axis; and
   b. a grid-like breast receiving pressure plate having a plurality of openings configured to slidably receive the guide block, each opening of the plurality of openings in the grid-like pressure plate having a central longitudinal axis concentric with the central longitudinal axis of the guide block when the guide block is slidably disposed in a predetermined one of the plurality of openings in the grid-like breast receiving pressure plate.

2. The guide block and grid-like breast receiving pressure plate assembly of claim 1 wherein at least a portion of the first passageway extends within the guide block away from the central longitudinal axis in a distal direction, the distal direction being from the proximal face toward the distal face, and configured such that the tissue removing device is guided by the first passageway in the distal direction from the proximal face toward the distal face toward the desired location.

3. The guide block and grid-like breast receiving pressure plate assembly of claim 1, wherein the first passageway extends within the guide block away from the central longitudinal axis in an acute angle in a distal direction, the distal direction being from the proximal face toward the distal face, and configured such that the tissue removing device is guided by the first passageway in the distal direction from the proximal face toward the distal face toward the desired location.

4. The guide block and grid-like breast receiving pressure plate assembly of claim 1, wherein the first passageway is oriented to intersect the central longitudinal axis within the guide block.

5. A guide block and grid-like breast receiving pressure plate assembly for a tissue removing device, comprising:
   a. a guide block having a proximal face with at least a first proximal opening, a distal face with at least a first distal opening, a body length between the proximal and distal faces with a central longitudinal axis extending within the guide block between the proximal and distal faces, a first passageway configured to extend within the guide block between the first proximal opening in the proximal face and the first distal opening in the distal face, the first passageway being oriented at an angle with respect to the central longitudinal axis that is not parallel to the central longitudinal axis; and
   b. a grid-like breast receiving pressure plate having a plurality of openings configured to slidably receive the guide block, each opening of the plurality of openings in the grid-like pressure plate having a central longitudinal axis concentric with the central longitudinal axis of the guide block when the guide block is slidably disposed in a predetermined one of the plurality of openings in the grid-like breast receiving pressure plate, the guide block configured such that the first proximal opening is entirely spaced away from the central longitudinal axis, the first distal opening is entirely spaced away from the central longitudinal axis, and the first passageway intersects the central longitudinal axis in an interior of the guide block between the proximal face and the distal face.

6. The guide block and grid-like breast receiving pressure plate assembly of claim 1, the guide block configured such that the first proximal opening located at the proximal face does not intersect the central longitudinal axis, the first distal opening located at the distal face does not intersect the central longitudinal axis, and the first passageway intersects the central longitudinal axis in an interior of the guide block between the proximal face and the distal face.

* * * * *